(12) United States Patent
Roffman et al.

(10) Patent No.: US 6,554,425 B1
(45) Date of Patent: Apr. 29, 2003

(54) OPHTHALMIC LENSES FOR HIGH ORDER ABERRATION CORRECTION AND PROCESSES FOR PRODUCTION OF THE LENSES

(75) Inventors: Jeffrey H. Roffman, Jacksonville, FL (US); Richard J. Nason, Roanoke, VA (US); Edgar V. Menezes, Roanoke, VA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 09/690,651

(22) Filed: Oct. 17, 2000

(51) Int. Cl.[7] .............................. G02C 7/06; G02C 7/04
(52) U.S. Cl. ...................... 351/177; 351/161; 351/168
(58) Field of Search ............................. 351/159, 160 R, 351/160 H, 161, 177

(56) References Cited

U.S. PATENT DOCUMENTS

| | | | |
|---|---|---|---|
| 4,787,733 A | * 11/1988 | Silva | 351/177 |
| 5,050,981 A | 9/1991 | Roffman | 351/177 |
| 5,114,628 A | 5/1992 | Hofer et al. | |
| 5,682,223 A | 10/1997 | Menezes et al. | |
| 5,777,719 A | 7/1998 | Williams et al. | 351/212 |
| 5,815,239 A | 9/1998 | Chapman et al. | 351/177 |
| 5,822,091 A | 10/1998 | Baker | 359/10 |
| 5,953,098 A | 9/1999 | Lieberman et al. | |
| 6,086,204 A | 7/2000 | Magnante | 351/212 |
| 6,095,651 A | 8/2000 | Wlliams et al. | 351/246 |
| 6,145,987 A | * 11/2000 | Baude et al. | 351/177 |

FOREIGN PATENT DOCUMENTS

| WO | WO 92/01417 A1 | 2/1992 |
|---|---|---|
| WO | WO 99/27334 | 6/1999 |

OTHER PUBLICATIONS

PCT Search Report—Application PCT/US 01/29540—Date of Mailing May 10, 2002.

* cited by examiner

Primary Examiner—Scott J. Sugarman
(74) Attorney, Agent, or Firm—Lois Gianneschi

(57) ABSTRACT

The invention provides multifocal ophthalmic lenses that have zones of more than one optical power, or focal length. The lenses correct for high order optical aberrations in more than one field of gaze.

29 Claims, 2 Drawing Sheets

OPHTHALMIC LENSES FOR HIGH ORDER ABERRATION CORRECTION AND PROCESSES FOR PRODUCTION OF THE LENSES

FIELD OF THE INVENTION

The invention relates to multifocal ophthalmic lenses. In particular, the invention provides lenses that have zones of more than one optical power, or focal length. The lenses correct for high order optical aberrations in more than one field of gaze.

BACKGROUND OF THE INVENTION

As an individual ages, the eye is less able to accommodate, or bend the natural lens, to focus on objects that are relatively near to the observer. This condition is known as presbyopia. Similarly, for persons who have had their natural lens removed and an intraocular lens inserted as a replacement, the ability to accommodate is absent.

Among the methods used to correct for the eye's failure to accommodate are lenses that have more than one optical power. In particular, spectacle, contact and intraocular lenses have been developed in which zones of distance, near, and intermediate power are provided. These lenses are disadvantageous because they only provide correction for low order optical aberrations, such as defocus and astigmatism, leaving higher order aberrations uncorrected. Thus, a need exists for a multifocal lens capable of correcting higher order optical aberrations.

Figure 1:
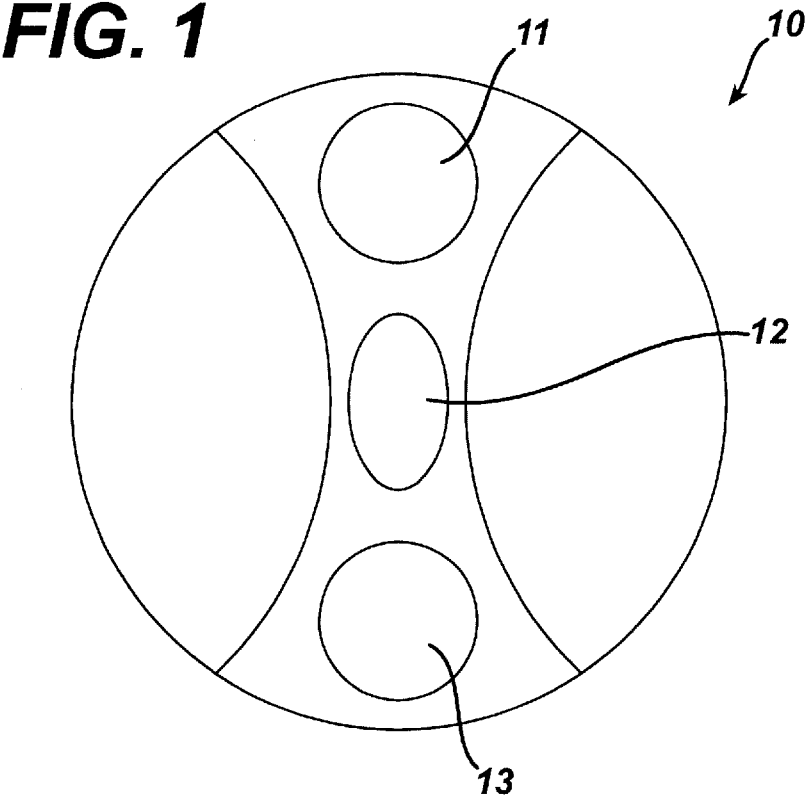
FIG. 1 is a top plan view of an embodiment of the lens of the invention.

Detailed Description of the Invention and Preferred Embodiments

The invention provides a multifocal lens, and methods for producing the lens, which lens corrects optical aberrations of the lens wearer's eye. These aberrations, generally, are any departure from a spherical wavefront at any position on the wavefront. The classic description of these aberrations are spherical aberration, astigmatism, coma, and distortion. Alternatively, the aberrations may be mathematically described, for example using Zernike polynomials. The lenses of the invention correct these aberrations in more than one direction of gaze.

In one embodiment, the invention provides a method for producing a lens for a lens wearer comprising, consisting essentially of, and consisting of the steps of a.) measuring the basic refractive prescription of the lens wearer; b.) measuring the wavefront aberrations of the lens wearer by providing visual targets at at least a first and a second distance; c.) converting the aberration measurements to a height difference; and d.) using the basic refractive prescription and converted difference to provide an ophthalmic lens for the lens wearer. By "lens" is meant a spectacle lens, a contact lens, an intraocular lens, a corneal implant lens, an onlay lens, and the like, or combinations thereof. Preferably, the lenses of the invention are spectacle or contact lenses.

In the first step of the invention, the basic refractive prescription of the lens wearer is measured by any conventional method or alternatively by ocular wavefront analysis. By "basic refractive prescription" is meant one or more of the distance vision, near vision, intermediate vision, cylinder power and prismatic power necessary to correct the lens wearer's vision.

The wavefront aberrations of the lens wearer's eye are then measured. By "wavefront aberrations" is meant the difference between the wavefront emerging from the eye compared to the wave front converging on the retina. In the method of the invention, the wavefront measurement is carried out by providing the lens wearer visual targets at at least two different distances, a first and a second distance. For example, one target may be provided in the lens wearer's distance vision zone, in which zone objects being viewed are about 15 feet or more from the eye. A second target may be provided in the near vision zone, in which zone an object being viewed is about 30 to about 50 cm from the eye. Preferably, a target also is provided in the lens wearer's intermediate vision zone, in which zone an object being viewed is about 50 to about 80 cm from the wearer's eye.

Apparatuses for performing the aberration measurements include, without limitation, aberroscopes, devices that measure ocular Modulation Transfer Function by point spread or line spread, or any similar devices that measure, estimate, interpolate, or calculate the ocular optical wavefront. An aberroscope capable of measuring the distance vision target is available from Wavefront Sciences, Inc, Albuquerque, N. Mex. It is well known in the art how to utilize such an aberroscope, as well as other devices available for aberration measurement, to measure targets at near and intermediate distances.

Once obtained, the aberration measurements then may be mathematically converted to a height difference thus providing an elevation map above and below a designated mean sphere value, known as the optical path difference. Correction for the aberrations will be provided by introduction of an optical path difference, or aberration inverse filter, that offsets the distortions due to the ocular aberrations.

The converted differences, along with the basic refractive prescription, and optionally corneal topographic data, are then used to provide a lens for the wearer. The data may be transformed onto a grid pattern of a rectilinear, polar concentric, or spiral format to correspond to the mechanism by which the surface of a lens or lens mold may be tooled using a computer numeric controlled ("CNC") lathe, direct machining of a polymer button, milling, laser ablation, injection molded insert or the like or a combination thereof. The required changes in the lens' surface elevation or slope to achieve correction of the aberrations may be incorporated onto the lens' front surface, back surface, or a combination thereof.

Figure 2:
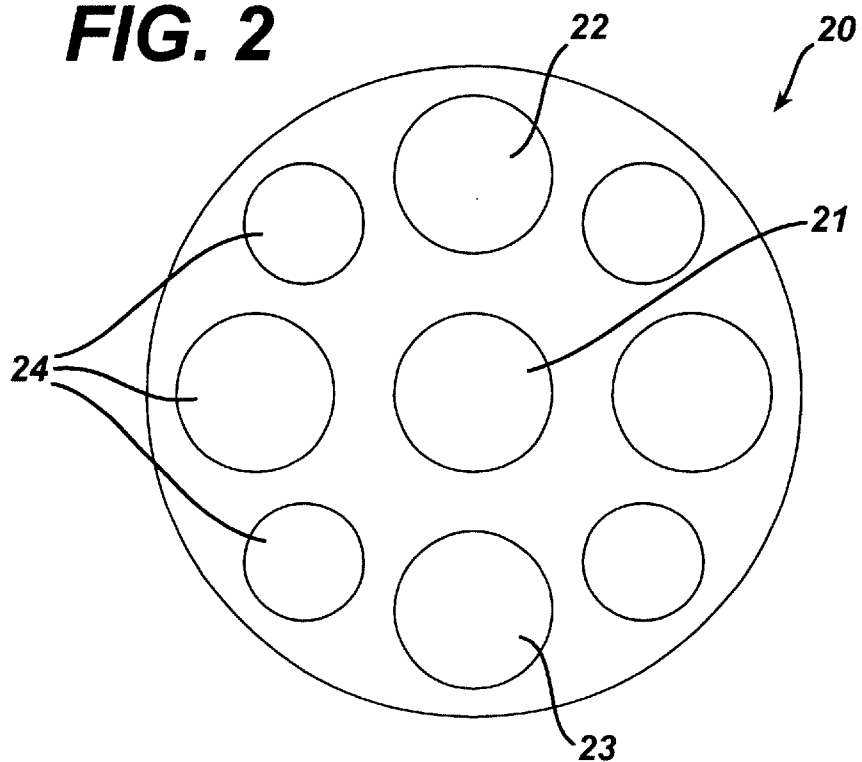
FIG. 2 is a top plan view of an embodiment of the lens of the invention.

In one embodiment, the lens is a spectacle lens with one surface on which there is a distance and near viewing zones, the distance zone produced to provide correction, including high order aberration correction, for the distance viewing region. Preferably, the high order aberration correction is located at the portion of the distance viewing zone most commonly used by the wearer's eye for distance viewing. Similarly, the near viewing zone may provide correction for the lens wearer's near vision including the aberrations. In FIG. 1 is shown spectacle lens 10 in which there are distance, intermediate, and near viewing zones 11, 12, and 13, respectively. An alternative embodiment is depicted in FIG. 2. Lens 20 of FIG. 2 is a single vision lens with central, top and bottom zones 21, 22, and 23, respectively, which zones correspond to the wearer's various directions of gaze. Additionally, a plurality of zones 24 are provided in the lens periphery, which zones control aberrations in the wearer's peripheral vision.

In any of the spectacle lens embodiments, aberration correction may be applied to one or both surfaces of the lens. The spectacle lenses may be formed by any known method including, without limitation, grinding of a lens blank, casting, molding, or combinations thereof. In a preferred embodiment, an optical preform having some or all of the basic refractive prescription is used and one or more surfaces are cast onto the optical preform to provide aberration correction and, optionally, additional basic refractive prescription power.

In another embodiment, the lens may be a contact lens. Preferably, the back, or concave, surface of the lens is a multifocal surface incorporating the basic refractive prescription of the lens wearer. The front, or convex, surface of the lens contains an optic zone that corrects the lens wearer's high order aberrations. Suitable multifocal surfaces are disclosed in U.S. Pat. Nos. 5,929,969, 5,835,192, 5,682,223, 5,485,228, and 5,448,312 incorporated in their entireties herein by reference. In an alternative embodiment, either or both of the basic refractive prescription and aberration correction may be divided between the front and back surfaces. In preferred embodiments, the back surface is matched to the wearer'corneal topography.

For lenses incorporating an inverse topographic elevation map of the lens wearers' cornea, the corneal topography may be determined by any known method including, without limitation, by use of a corneal topographer. For soft contact lens manufacture, the elevational data initially is applied to a lens model in the unflexed state. Next, the data is transformed by taking into account the soft lens flexure, or wrap, when the lens placed on the eye. Thus, the effects of both elevation of the cornea and wrap are accounted for when using the corneal topographic data. The flexure transformed data then may be mapped onto a CNC grid pattern and used to make the lenses or mold tool surface.

Figure 3A:
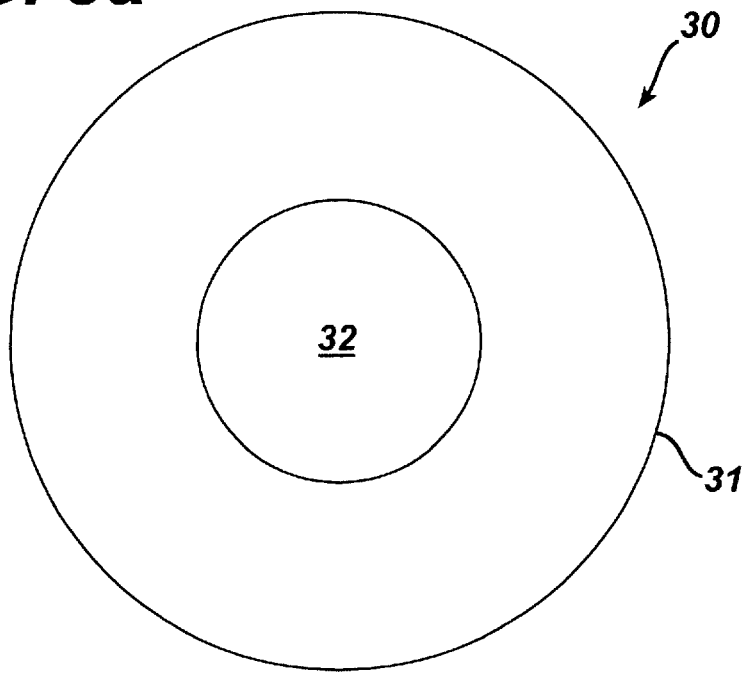
FIG. 3a is a top plan view of the convex surface of an embodiment of the lens of the invention.
Figure 3B:
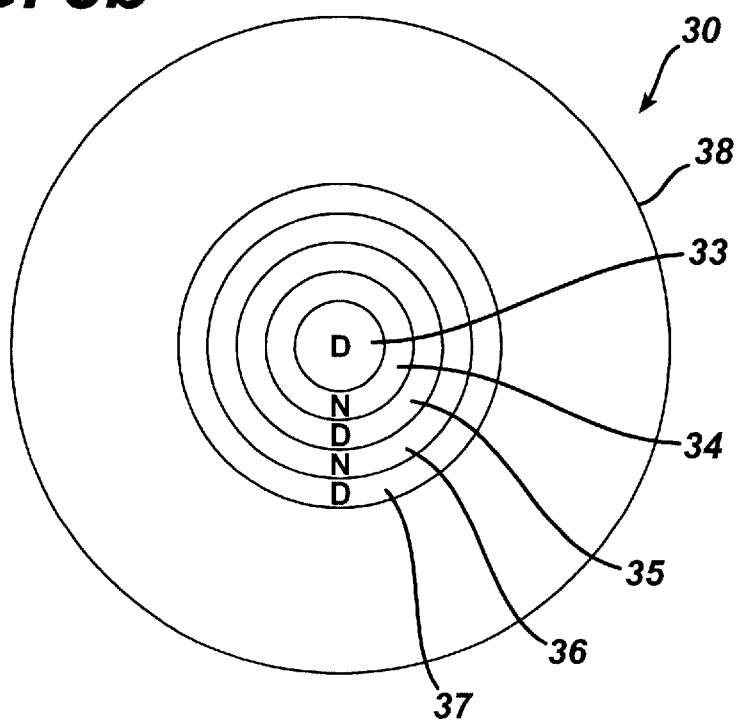
FIG. 3b is a top plan view of the concave surface of an embodiment of the lens of the invention.

FIGS. 3a and 3b depicts a contact lens 30 of the invention. The lens has a convex surface 31 with a central optic zone 32 with the desired distance optical power. By "distance optical power" is meant the amount of refractive power required to correct the wearer's distance vision acuity to the desired degree. The concave surface 38 has five concentric annular rings 33, 34, 35, 36 and 37 respectively, in the optic zone alternating near optical power and distance optical power. By "near optical power" is meant the amount of refractive power required to correct the wearer's near vision acuity to the desired degree. The aberration inverse filter may be applied to the front, back, or both surfaces of the lens. One or more rings of intermediate optical power may also be provided. The aberration inverse filter may be tailored to and specifically applied to one or more of the various distance and near vision zones.

Any number of variations of the lens of FIGS. 3a and 3b are possible. The central optic zone may have either distance or near optical power therein and may be on the concave or convex surface, but preferably is on the convex surface. The number of annular rings preferably is at least two, more preferably about 4 to about 7, and may be on the convex or concave lens surface, but preferably is on the concave surface.

A pair of contact lenses may be provided, one lens to be worn in the dominant eye and one to be worn in the non-dominant eye. By "dominant eye" is meant the eye that predominates for distance vision. The lens worn by the dominant eye has a convex surface with a central optic zone with the desired distance optical power. The concave surface has at least two concentric annular zones in its optic zone. The power of each of the at least two annular zones is substantially equal to that of the distance optical power. Either or both the convex and concave surfaces may have additional annular zones with distance optical power, near optical power, or combinations thereof. In this embodiment, preferably, the convex surface has only the central optical zone and no annular zones, the concave surface in this embodiment having at least two annular zones of either or both distance and near optical power. More preferably, the convex surface has only a central optical zone having the distance optical power, the concave surface having at least two zones of the distance optical power and one or more annular zones of near optical power.

The lens worn by the non-dominant eye has a convex surface with a central optic zone with the desired near optical power. The concave surface has at least two concentric annular zones in its optic zone. The power of each of the at least two annular zones is substantially equal to that of the near optical power. Either or both the convex and concave surfaces may have additional annular zones with distance optical power, near optical power, or combinations thereof. Preferably, the convex surface has only the central optical zone and no annular zones, the concave surface in this embodiment having at least two annular zones of either or both distance and near optical power. More preferably, the convex surface has only a central optical zone having the near optical power, the concave surface having at least two zones of the near optical power and one or more annular zones of distance optical power.

For the contact lenses of the invention, in those embodiments in which both distance and near optical power annular zones are used, the distance annular zones preferably alternate with the near annular zones. Additionally, cylinder power may be combined with either or both of the distance and near optical powers. One or more annular zones of intermediate power, or power between that of the near and distance power, also may be provided on either lens of the lens pair of the invention.

In those case in which both near and distance power annular zones are used in the contact lens for the dominant eye, the ratio of the lens' optic zone area devoted to the distance and near optical powers must be such that more area is devoted to the distance power. For the lens of the non-dominant eye, more lens area will be devoted to the near vision power. The preferred areas, on a percentage basis, for both the dominant and non-dominant eye lenses are disclosed in U.S. Pat. Nos. 5,835,192, 5,485,228, and 5,448,312.

Contact lenses useful in the invention may be either hard or soft lenses. Soft contact lenses, made of any material suitable for producing such lenses, preferably are used. The lenses of the invention may have any of a variety of corrective optical characteristics incorporated onto the surfaces in addition to aberration correction and distance and near optical powers, such as, for example, cylinder power.

The contact lenses of the invention may be formed by any conventional method. For example, the annular zones formed therein may produced by diamond-turning using alternating radii. The zones may be diamond-turned into the molds that are used to form the lens of the invention. Subsequently, a suitable liquid resin is placed between the molds followed by compression and curing of the resin to form the lenses of the invention. Alternatively, the zones may be diamond-turned into lens buttons.

In the case of an intraocular lens, the corneal topography data may be combined with wavefront both on the lens' front surface, back surface, or a combination thereof. The multifocal portion may be placed, along with aberration correction, on the front or back surface. Known methods for producing intraocular lenses then may be used to manufacture the lenses.

In all of the lenses of the invention, the distance, intermediate and near optical powers may be spherical or aspheric powers. Additionally, the distance and near optical power zones may be of any desired and practicable dimensions.

What is claimed is:

1. A method for producing a lens for a lens wearer comprising the steps of: a.) measuring the basic refractive prescription of the lens wearer; b.) measuring the wavefront aberrations of the lens wearer by providing visual targets at at least a first and a second distance; c.) converting the aberration measurements to a height difference; and d.) using the basic refractive prescription and converted difference to provide an ophthalmic lens for the lens wearer.

2. The method of claim 1, wherein the lens is a contact lens.

3. The method of claim 1, wherein the lens is a spectacle lens.

4. The method of claim 1, wherein the first distance comprises a distance of about 15 feet or more from the eye and the second distance comprises a distance of about 30 to about 50 cm from the eye.

5. The method of claim 4, wherein step b.) further comprises measuring the wavefront aberrations of the lens wearer by providing a visual target at a distance that is about 50 to about 80 cm from the wearer's eye.

6. The method of claim 1, wherein step d.) further comprises incorporating changes in the elevation of the lens' front surface, back surface, or a combination thereof to achieve correction of the wavefront aberrations.

7. The method of claim 6, wherein the lens is a spectacle lens and step d.) is carried out by providing the lens with one surface comprising distance and near viewing zones, wherein the distance zone is produced to provide wavefront aberration correction, for distance viewing.

8. The method of claim 7, wherein the wavefront aberration correction is located at a portion of the distance viewing zone most commonly used by the wearer's eye for distance viewing.

9. The method of claim 7 or 8, further comprising providing wavefront aberration correction for the near viewing zone.

10. The method of claim 9 wherein step d.) further comprises providing a plurality of zones in the lens periphery wherein the plurality of zones provide wavefront aberration control for the wearer's peripheral vision.

11. The method of claim 6, wherein the lens is a contact lens and step d.) further comprises providing the lens with a first surface that is a multifocal surface comprising the basic refractive prescription of the lens wearer and a second surface comprising an optic zone that provides correction for wavefront aberrations.

12. The method of claim 11, wherein the first surface is the concave surface.

13. The method of claim 11, wherein step d.) further comprises matching the concave surface to the wearer's corneal topography.

14. The method of claim 6, wherein the lens is a contact lens and step d.) further comprises distributing the basic refractive prescription, the wavefront aberration correction, or both between the first and second surfaces.

15. The method of claim 14, wherein the distribution is of the basic refractive prescription.

16. The method of claim 14, wherein the distribution is of the wavefront aberration correction.

17. The method of claim 14, wherein the distribution is of both the basic refractive prescription and the wavefront aberration correction.

18. A multifocal lens, comprising a front surface, back surface, or a combination thereof wherein changes in the elevation of the lens' surface are incorporated in order to achieve correction of the wavefront aberrations.

19. The lens of claim 18, wherein the lens is a spectacle lens comprising a first surface comprising distance and near viewing zones, wherein the distance zone is produced to provide wavefront aberration correction, for distance viewing.

20. The lens of claim 19, wherein the wavefront aberration correction is located at a portion of the distance viewing zone most commonly used by the wearer's eye for distance viewing.

21. The lens of claim 19 or 20, wherein the near viewing zone comprises wavefront aberration correction.

22. The lens of claim 21 wherein at least one the lens surfaces further comprises a plurality of zones in the lens periphery wherein the plurality of zones provide wavefront aberration control for the wearer's peripheral vision.

23. The lens of claim 18, wherein the lens is a contact lens comprising a first surface that is a multifocal surface comprising the basic refractive prescription of the lens wearer and a second surface comprising an optic zone comprising correction for wavefront aberrations.

24. The lens of claim 23, wherein the first surface is the concave surface.

25. The lens of claim 24, wherein the concave surface substantially matches the lens wearer's corneal topography.

26. The lens of claim 18, wherein the lens is a contact lens wherein the basic refractive prescription, the wavefront aberration correction, or both are distributed between the first and second surfaces.

27. The lens of claim 26, wherein the distribution is of the basic refractive prescription.

28. The lens of claim 26, wherein the distribution is of the wavefront aberration correction.

29. The method of claim 26, wherein the distribution is of both the basic refractive prescription and the wavefront aberration correction.

* * * * *